United States Patent [19]

Bauer et al.

[11] Patent Number: 4,918,221
[45] Date of Patent: Apr. 17, 1990

[54] PROCESS FOR PREPARING 2,5-DICHLOROPHENYLTHIOGLYCOLLIC ACID

[75] Inventors: Wolfgang Bauer, Maintal; Willi Steckelberg, Hofheim, both of Fed. Rep. of Germany

[73] Assignee: Cassella AG, Frankfurt am Main, Fed. Rep. of Germany

[21] Appl. No.: 186,638

[22] Filed: Apr. 27, 1988

[30] Foreign Application Priority Data

May 9, 1987 [DE] Fed. Rep. of Germany ....... 3715508

[51] Int. Cl.$^4$ ........................................... C07C 149/40
[52] U.S. Cl. .................................................. 562/431
[58] Field of Search ............. 558/4; 562/431; 560/17; 568/65

[56] References Cited

U.S. PATENT DOCUMENTS 4,461,911 7/1984 Schütze et al. .................. 560/18

FOREIGN PATENT DOCUMENTS 1183696 1/1969 United Kingdom .

OTHER PUBLICATIONS

Gundermann et al., Methoden der Organischen Chemie, vol. E11, p. 56 (1985).

*Primary Examiner*—Michael L. Shippen
*Attorney, Agent, or Firm*—Connolly and Hutz

[57] ABSTRACT

A valuable starting material for the manufacture of tetrachlorothioindigo pigments is 2,5-dichlorophenyl-thioglycollic acid which is prepared by:
(a) diazotizing 2,5-dichloroaniline with aqueous alkali metal nitrite at acidic pH to produce 2,5-dichlorophenyl-diazonium salt,
(b) reacting the 2,5-dichlorophenyl-diazonium salt from (a) with thiourea in an aqueous medium at acidic pH in the presence of a catalyst to produce 2,5-dichlorophenyl-isothiuronium salt of the formula

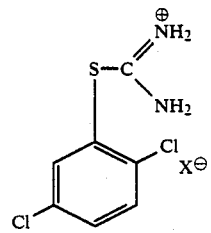

wherein $X^{\ominus}$ is an anion of a mineral acid,
(c) hydroloyzing the 2,5-dichlorophenylisothi-uronium salt from (b), without intermediate isolation, at alkaline pH to produce 2,5-dichlorothiophenol and
(d) condensing the 2,5-dichlorothiophenol with monochloroacetic acid to produce 2,5-dichlorophenylthioglycollic acid.

6 Claims, No Drawings

PROCESS FOR PREPARING 2,5-DICHLOROPHENYLTHIOGLYCOLLIC ACID

The present invention relates to a novel, economically and ecologically advantageous process for preparing 2,5dichlorophenylthioglycollic acid of the formula IV by reacting 2,5-dichlorophenyl-diazonium salts of the formula I, wherein $X^{\ominus}$ the anion of a mineral acid, with thiourea in the presence of a catalyst to give 2,5-dichlorophenyl-isthiuronium salts of the formula II and subsequent hydrolysis to 2,5dichlorothiophenol of the formula III and condensation with monochloroacetic acid:

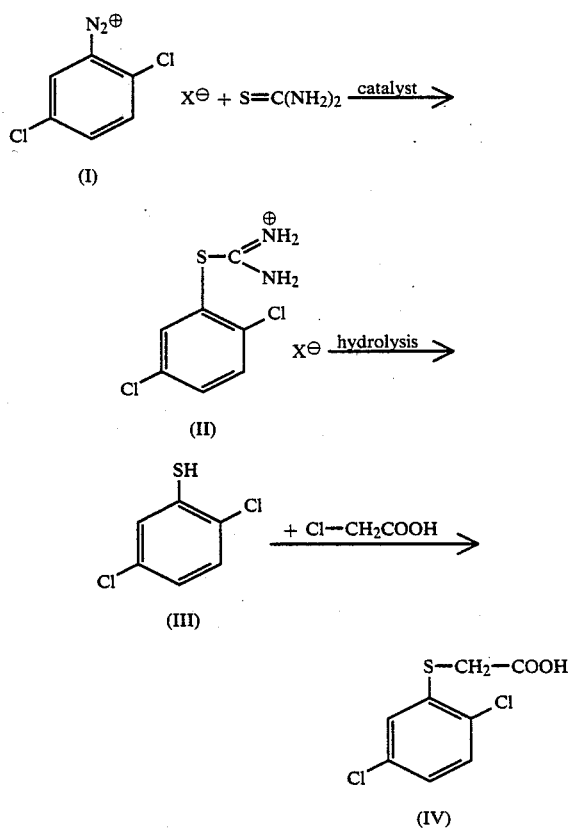

2,5-Dichlorophenylthioglycollic acid is a valuable starting material for the preparation of tetrachlorothioindigo pigment.

Various processes for the synthesis of 2,5-dichlorophenylthioglycollic acid are already known, according to which 2,5-dichlorophenyl-diazanium salts are reacted with thioglycollic acid.

Thus, for example, a process is described in EP-A 67,352, (corresponding to U.S. Pat. No. 4,461,911), according to which aryldiazonium salts, for example, 2,5-dichlorophenyl-diazonium salts, are converted with thioglycollic acid in an aqueous acidic medium into S-arylthioglycollic acids, for example 2,5-dichlorophenylthioglycollic acid. Although this process is an improvement over previously described processes for preparing S-arylthioglycollic acids (German Patent Specification 194,040, German Patent Specification 201,231, German Patent Specification 201,232 and Swiss Patent Specification 451,921 - corresponding the U.S. Pat. No. 3,419,606) with respect to the obtainable yield of 75 to 84% of theory, considerable disadvantages arise from the required use of uneconomically large amounts of copper salts, preferably 0.6 to 1 mol of copper salt per mol of aryldiazonium salt.

The resulting production effluents have a high content of copper salts, which either must be removed by involved, cost-intensive reprocessing methods or represent considerable pollution of the environment.

Moreover, the S-arylthioglycollic acids obtained initially must be further purified by involved methods.

According to a further process described in German Offenlegungsschrift 3,309,142, S-arylthioglycollic acids are prepared by reacting aryldiazonium salts with thioglycollic acid in a mixture of water and an organic solvent which is miscible with water only partially or not at all, such as chloroform, o-dichlorobenzene; trichloroethylene and, in particular, perchloroethylene.

The use of these chlorinated hydrocarbons raises various problems, in particular in connection with cost-intensive methods for purifying the exit air in filtration steps and in the solvent regeneration. Moreover, the said process involves the risk of effluent pollution by the chlorinated hydrocarbons employed.

A further method for preparing 2,5-dichlorophenylthioglycollic acid comprises the sulphochlorination of 1,4-dichlorobenzene with chlorosulphonic acid and thionyl chloride to give 2,5-dichlorobenzenesulphochloride, subsequent reduction of 2,5-dichlorobenzenesulphochloride with a large excess of zinc powder in a medium containing sulphuric acid (see, for example, British Patent Specification 1,183,696; Monatshefte für Chemie 48, 627 (1927); Organic Syntheses, Coll.Vol.I, 504 (1964)) to give 2,5-dichlorothiophenol which, in a subsequent step, is condensed with monochloroacetic acid to give 2,5-dichlorophenylthioglycollic acid (British Patent Specification 1,183,696).

This process is also affected by a number of disadvantages in an ecological and economical respect, which arise above all from the high effluent pollution load due to dilute acid in the isolation of 2,5-dichlorobenzenesulphochloride and, in the reduction step, due to considerable quantities of heavy metal salts in the zinc dust reduction.

The handling of finely disperse zinc dust in the presence of nascent hydrogen evolved during the zinc dust reduction also causes safety problems.

Accordingly, it was the object of the present invention to provide an environmentally acceptable process for preparing 2,5-dichlorophenylthioglycollic acid which does not involve the economic and ecological problems of the processes already known.

Surprisingly, this object can be achieved when 2,5-dichlorophenyl-diazonium salts of the formula I are converted with thiourea in an aqueous medium at acidic pH values in the presence of a catalyst into 2,5-dichlorophenyl-isothiuronium salts of the formula II, these are hydrolysed, without intermediate isolation, at alkaline pH values to give 2,5-dichlorothiophenol of the formula III and the latter is condensed with monochloroacetic acid in a manner known per se to give 2,5-dichlorophenylthioglycollic acid of the formula IV.

The reaction of the 2,5-dichlorophenyl-diazonium salts of the formula I with thiourea is carried out in an aqueous medium at acidic pH values from 0 to 6.5, preferably from 0 to 4. The reaction temperatures are as a rule between $-10°$ and $+50°$ C., preferably between $0°$ and $30°$ C. In general, 1 to 1.4 mol, preferably 1 to 1.25 mol, of thiourea and, as the catalyst, 0.001 to 0.05 mol, preferably 0.01 to 0.03 mol, of a copper(I) or copper(II) salt are employed per mol of 2,5-dichlorophenyl-diazonium salt of the formula I.

The hydrolysis of the 2,5-dichlorophenyl-isothiuronium salts of the formula II is as a rule carried out at temperatures between 30 and 130° C., preferably 60 and 100° C. The 2,5-dichlorothiophenol thus formed, of the formula III, can then be isolated as an intermediate, for example by steam distillation or extraction.

In a preferred embodiment of the process according to the invention, 2,5-dichlorothiophenol is converted, without intermediate isolation, by condensation with chloroacetic acid into 2,5-dichlorophenylthioglycollic acid as the end product.

A particularly preferred embodiment of the process according to the invention comprises adding finely disperse, non-metallic solid substances, which are insoluble and inert under the reaction conditions, to the catalyst.

As a result, the yield of 2,5-dichlorophenylthioglycollic acid is even further increased and the formation of undesired by-products is reduced.

Examples of suitable finely dispense, non-metallic solid substances are all water-insoluble synthetic or natural materials which are used as adsorbants in industrial adsorption processes or in adsorption chromatography, such as, for example, activated carbons, animal charcoals and bone charcoals, silicates and aluminium silicates such as, for example, silica (silica gel), kieselguhr, bleaching earths, bentonites, montmorillonite, aluminas, bauxites, talc, glass powder and molecular sieves. Water-insoluble oxides and salts, for example carbonates, silicates or sulphates of alkaline earth metals, are, for example, also suitable.

Such finely disperse substances used in the process according to the invention have a specific surface area of preferably greater than 0.06 $m^2/cm^3$.

In a 1 molar batch, they are as a rule employed in quantities from 1 to 20 g, preferably 5 to 15 g. They can be used alone or as a mixture with one another.

A very particularly preferred embodiment of the process according to the invention comprises using, as the catalyst, catalytic quantities of copper(I) salts or copper(II) salts, to which the said finely disperse substances have been added.

The copper salts employed in catalytic quantities can be precipitated as copper sulphide by the addition of equimolar quantities of sodium sulphide or sodium hydrogen sulphide and removed by a filtration step before the isolation of the 2,5-dichlorophenylthioglycollic acid, in which case production effluents arise which are free of heavy metal salts.

In the process according to the invention the yield of 2,5-dichlorophenylthioglycollic acid is about 83 to 90% of theory, relative to 2,5-dichlorophenyl-diazonium salts, which is surprising in view of the multi-stage process, above all because it is described in the literature (K.-D. Gundermann and K. Hümke, in Houben-Weyl, Methoden der Organischen Chemie [Methods of Organic Chemistry], volume E 11, page 56 (1985)) that chloro-substituted aryldiazonium salts and thiourea, with subsequent hydrolysis of the aryl-isothiuronium chlorides formed as intermediates, give the corresponding chlorosubstituted thiophenols in a yield of only 22 to 50% of theory.

EXAMPLE 1

162 g of 2,5-dichloroaniline are introduced into a mixture of 500 ml of water and 350 ml of 10 N hydrochloric acid and diazotized in the conventional manner at 0° to 5° C. with a solution of 76 g of sodium nitrite in 150 ml of water. The resulting solution of 2,5-dichlorophenyl-diazonium chloride is then run in at a temperature of 10° to 15° C. into a well stirred mixture of 91.2 g of thiourea, 5 g of copper(II) sulphate pentahydrate and 5 g of Corlite ® in 500 ml of water. The mixture is stirred for approximately 1 further hour, the pH value is raised to 8.5 by means of 330 ml of 10 N sodium hydroxide solution and the mixture is hydrolysed for 1 hour at 90° C. The pH value is then adjusted to 3 by means of 10 N hydrochloric acid and the resulting 2,5-dichlorothiophenol is isolated by steam distillation. (Corlite ® is a registered trademark of Corneco-Chemie GmbH., Dortmund) Yield: 154 g of 2,5-dichlorothiophenol (86% of theory), Boiling point: 126° to 129° C./10 mbar.

154 g of 2,5-dichlorothiophenol are introduced into 1.8 liters of water, and 200 ml of 10 N sodium hydroxide solution and then, at 80° C., 104 g of monochloroacetic acid are added. The product is then precipitated at 40° to 50° C. by means of 124 ml of 10 N hydrochloric acid, isolated by filtration, washed with water until free of acid and dried at 80° C. Yield: 194.4 g of 2,5-dichlorophenylthioglycollic acid (82 % of theory, relative to 2,5-dichloroaniline); melting point: 130° to 132° C.

EXAMPLE 2

A 2,5-dichlorophenyl-diazonium chloride solution, prepared according to Example 1 from 162 g of 2,5-dichloroaniline, is added at 10° to 15° C. to a mixture of 81.2 g of thiourea, 5 g of copper(II) sulphate pentahydrate, 5 g of activated carbon and 10 g of Corlite ® in 500 ml of water.

After the evolution of nitrogen has ceased, the pH value is adjusted to 8.5 by addition of 330 ml of 10 N sodium hydroxide solution, the mixture is heated for 1 hour at 90° C., and 200 ml of 10 N sodium hydroxide solution, 800 ml of water and 128.8 g of monochloroacetic acid are then added. The mixture is heated to 100° C., treated with 2.6 g of 60% sodium sulphide and filtered. The isolation of the product from the alkaline filtrate is carried out by adding 10 N hydrochloric acid up to a pH value of 2, filtration at 20° C., washing until neutral and drying at 80° C. Yield: 211 g of 2,5-dichlorophenylthioglycollic acid (89 % of theory relative to 2,5-dichloroaniline); melting point: 129° to 131° C.

The resulting filtrate has a copper content of <1 ppm.

EXAMPLE 3

Reaction according to Example 2, but without the use of activated carbon and Corlite ®.

Yield: 197 g of 2,5-dichlorophenylthioglycollic acid (83% of theory, relative to 2,5-dichloroaniline); melting point: 126° to 129° C.

The table which follows shows further examples of the preparation of 2,5-dichlorophenylthioglycollic acid by the process according to the invention. In these cases, the procedure followed is as described in Example 2, but with the use of the catalysts listed in column 2. The indicated quantities relate to 1 mol of 2,5-dichloroaniline.

| Example | Catalyst | 2,5-dichlorophenylthioglycollic acid Yield (% of theory) | Melting point (°C.) |
|---|---|---|---|
| 4 | 2.7 g of copper (II) chloride 15 g of Corlite ® | 86 | 128 to 130 |
| 5 | 2.5 g of copper (I) chloride 7.5 g of activated carbon | 85 | 127 to 130 |
| 6 | 5 g of copper (II) sulphate pentahydrate 2.5 g of activated carbon 2.5 g of alumina | 84 | 127 to 130 |
| 7 | 5 g of copper (II) sulphate pentahydrate 4 g of activated carbon 8 g of silica gel | 88 | 128 to 131 |

What is claimed is:

1. The process for preparing 2, 5-dichlorophenylthioglycollic acid which comprises:
   (a) diazotizing 2,5-dichloroaniline with aqueous alkali metal nitrite at acidic pH to produce 2,5-dichlorophenyl-diazonium salt,
   (b) reacting the 2,5-dichlorophenyl-diazonium salt from (a) with thiourea in an aqueous medium at acidic pH in the presence of a catalyst, and optionally in the presence of a finely dispersed non-metallic adsorbant, to produce 2,5-dichlorophenyl-isothuronium salt of the formula

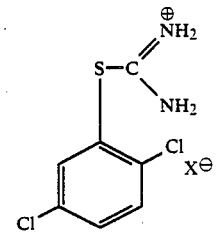

wherein $X^\ominus$ is an anion of a mineral acid,
   (c) hydroloyzing the 2,5-dichlorophenylisothiuronium salt from (b), without intermediate isolation, at alkaline pH to produce 2,5-dichlorothiophenol and
   (d) condensing the 2,5-dichlorothiophenol with monochloroacetic acid to produce 2,5-dichlorophenylthioglycollic acid.

2. The process according to claim 1 wherein copper(I) salts or copper(II) salts are the catalyst of step (b).

3. The process according to claim 1 wherein the catalyst of step (b) is 0.001 to 0.05 mol of copper(I) salt or copper (II) salt and 1 to 20 grams of a finely dispersed, non-metallic adsorbant per mol of 2,5-dichlorophenyldiazonium salt.

4. The process according to claim 3 wherein the catalyst of step (b) is 0.001 to 0.03 mol of copper salt and 5 to 15 grams of non-metallic solid substance per mol of 2,5-dichlorophenyl-diazonium salt.

5. The process according to claim 1 wherein 1 to 1.4 mol of thiourea per mol of 2,5-dichlorophenyl-diazonium salt are reacted in step (b).

6. The process according to claim 5 wherein the amount of thiourea is 1 to 1.25 mol per mol of 2,5-dichlorophenyl-diazonium salt.

* * * * *